(12) United States Patent
Heser et al.

(10) Patent No.: US 11,717,377 B2
(45) Date of Patent: Aug. 8, 2023

(54) MEDICAL DEVICE SUPPORT SYSTEM INCLUDING ROTATIONAL CONTROL MECHANISM

(71) Applicant: American Sterilizer Company, Mentor, OH (US)

(72) Inventors: Michael Joseph Heser, Willoughby, OH (US); Jerime Josef Pichler, Painesville, OH (US)

(73) Assignee: American Sterilizer Company, Mentor, OH (US)

( * ) Notice: Subject to any disclaimer, the term of this patent is extended or adjusted under 35 U.S.C. 154(b) by 49 days.

(21) Appl. No.: 17/551,504

(22) Filed: Dec. 15, 2021

(65) Prior Publication Data

US 2022/0211462 A1    Jul. 7, 2022

Related U.S. Application Data

(60) Provisional application No. 63/134,263, filed on Jan. 6, 2021, provisional application No. 63/134,254, filed (Continued)

(51) Int. Cl.
*A61B 90/50*     (2016.01)
*A61B 90/35*     (2016.01)
(Continued)

(52) U.S. Cl.
CPC .............. *A61B 90/50* (2016.02); *A61B 90/03* (2016.02); *A61B 90/35* (2016.02); *F21V 21/28* (2013.01);
(Continued)

(58) Field of Classification Search
CPC ......... A61B 90/50; A61B 90/03; A61B 90/35; A61B 2090/035; A61B 2090/508; F21V 21/28
See application file for complete search history.

(56) References Cited

U.S. PATENT DOCUMENTS 3,240,925 A    3/1966   Kaschke et al.
6,471,363 B2  10/2002   Howell et al.
(Continued)

FOREIGN PATENT DOCUMENTS

WO       2020/159616 A1     8/2020

OTHER PUBLICATIONS

International Search Report and Written Opinion for corresponding PCT International Application No. PCT/US2021/063478, completion date Mar. 11, 2022.

*Primary Examiner* — Anita M King
(74) *Attorney, Agent, or Firm* — Renner, Otto, Boisselle & Sklar, LLP

(57) ABSTRACT

A medical device support system including a shaft, an extension arm, and a hub mounted to the shaft for pivotable movement of the extension arm about a rotation axis of the shaft. The hub includes a cavity including first and second contact faces, and at least one floating stop movably disposed in the cavity. The hub is pivotably mounted for a range of at least 360-degrees rotation about the rotation axis. The at least 360-degrees rotation range is based on a compound of a first rotation range and a second rotation range. The first rotation range is defined by a first movable amount of the at least one floating stop between first and second stop surfaces fixed relative to the shaft. The second rotation range is defined by a second movable amount of the at least one floating stop between the first and second contact faces of the hub.

20 Claims, 11 Drawing Sheets

Related U.S. Application Data on Jan. 6, 2021, provisional application No. 63/134,248, filed on Jan. 6, 2021.

(51) Int. Cl.
*F21V 21/28* (2006.01)
*A61B 90/00* (2016.01)

(52) U.S. Cl.
CPC ... *A61B 2090/035* (2016.02); *A61B 2090/508* (2016.02)

(56) References Cited

U.S. PATENT DOCUMENTS

| | | |
|---|---|---|
| 8,070,331 B2 | 12/2011 | Gull et al. |
| 8,757,345 B2 | 6/2014 | Blank et al. |
| 8,899,834 B2 | 12/2014 | Barker et al. |
| 9,239,127 B2 | 1/2016 | Kronung |
| 9,945,498 B2 | 4/2018 | Timoszyk et al. |
| 10,835,346 B2 * | 11/2020 | Bellows ............... F16D 65/065 |
| 10,874,476 B2 * | 12/2020 | Bellows ............... A61B 50/28 |
| 10,993,778 B2 * | 5/2021 | Bellows ............... F16D 65/065 |
| 11,173,009 B2 * | 11/2021 | Bellows ............... A61B 90/50 |
| 11,547,522 B2 * | 1/2023 | Moss ............... F16M 13/022 |
| 2020/0030055 A1 * | 1/2020 | Bellows ............... A61B 50/28 |
| 2020/0030056 A1 | 1/2020 | Bellows et al. |
| 2020/0306006 A1 | 10/2020 | Bellows et al. |
| 2022/0211461 A1 * | 7/2022 | Heser ............... E05D 11/06 |
| 2022/0211463 A1 * | 7/2022 | Heser ............... F16D 49/08 |

* cited by examiner

MEDICAL DEVICE SUPPORT SYSTEM INCLUDING ROTATIONAL CONTROL MECHANISM

RELATED APPLICATIONS

This application claims the benefit of U.S. Provisional Application No. 63/134,248, filed Jan. 6, 2021, U.S. Provisional Application No. 63/134,254, filed Jan. 6, 2021, U.S. Provisional Application No. 63/134,263, filed Jan. 6, 2021, which are hereby incorporated herein by reference in their entireties.

FIELD OF INVENTION

This application relates generally to a rotational control mechanism for a medical device suspension system or carry system for use in, for example, a hospital examination room, a clinic, a surgery room or an emergency room, and more particularly to a rotational control mechanism that simplifies rotational control of an extension arm about a shaft of the medical device support system and provides at least 360° (360-degrees) rotation of the extension arm about the shaft.

BACKGROUND

Medical device suspension systems or carry systems are used in health treatment settings such as hospital examination rooms, clinics, surgery rooms and emergency rooms. These systems may suspend or support any variety of medical devices or components including surgical lights, supply consoles, patient monitors, camera detector heads, medical instruments, ventilator systems, suction devices, among others. The systems typically include a shaft or support spindle that is suspended from the ceiling or mounted to a wall or stand, and one or more generally horizontal extension arms mounted for rotational movement about the shaft. Each extension arm typically has a hub at its proximal end mounted to the shaft for pivotable movement about the shaft, and a support at its distal end for supporting a medical device. The extension arm can be rotatably adjusted about the shaft to a desired angular position to provide appropriate access to medical devices and components associated with the arm.

It is desirable to limit the rotation of the extension arm about the shaft for example to prevent collision of medical devices at the distal ends of the arms, or to prevent undue strain on electrical or communication lines passing through the shaft and the extension arm. In most current support systems, the extension arm is equipped with a fixed feature in the hub that contacts a fixed feature on the shaft that prevents further rotation.

For rotational control mechanisms in some medical device suspension systems or carry systems, there remain various shortcomings, drawbacks, and disadvantages relative to certain applications. For example, in some systems the rotational control mechanism limits rotation of the extension arm to below 360° (360-degrees), which may limit options for some installations. Other rotational control mechanisms require multiple stacked components, which increase the volumetric footprint of the mechanisms and complicates their integration into the hub of the extension arm.

Accordingly, there remains a need for further contributions in this area of technology.

SUMMARY OF INVENTION

The application relates to a rotational control mechanism for a medical device support system, in which the rotational control mechanism enables at least 360° (360-degrees) rotation of the extension arm about the shaft, and also embodies fewer components and a smaller volumetric footprint than heretofore attained, thus simplifying and adding efficiency to the factory assembly and field service of the medical device support system.

According to one aspect of the invention, a medical device support system includes a shaft, an extension arm, and at least one floating stop. The extension arm may have a support for a medical device. A hub at a proximal end of the extension arm may be mounted to the shaft for pivotable movement of the extension arm and the hub about a rotation axis of the shaft. The hub may have an elongated cavity including first and second contact faces. The at least one floating stop may be movably disposed in the elongated cavity of the hub between the first and second contact faces. The hub may be pivotably mounted for a range of at least 360-degrees rotation about the rotation axis, wherein the at least 360-degrees rotation range is based on a compound of a first rotation range and a second rotation range, wherein the first rotation range is defined by a first movable amount of the at least one floating stop between first and second stop surfaces fixed relative to the shaft, and wherein the second rotation range is defined by a second movable amount of the at least one floating stop between the first and second contact faces of the hub.

Embodiments of the invention may include one or more of the following additional features separately or in any combination.

The at least one floating stop interfacing with one of the first or second stop surfaces of the shaft and one of the first or second contact faces of the hub may restrict rotation of the hub about the rotation axis beyond the at least 360-degrees rotation range.

The hub may be pivotably mounted for the at least 360-degrees rotation from a first stop position to a second stop position and vice versa, wherein at the first stop position, the at least one floating stop interfaces with one of the first or second stop surfaces fixed relative to the shaft and one of the first or second contact faces of the hub to limit further counterclockwise rotation of the hub about the rotation axis, and at the second stop position, the at least one floating stop interfaces with an opposite one of the first or second stop surfaces and an opposite one of the first and second contact faces of the hub to limit further clockwise rotation of the hub about the rotation axis.

The at least one floating stop may be sandwiched between the first stop surface and the first contact face at the first stop position, and the at least one floating stop may be sandwiched between the second stop surface and the second contact face at the second stop position.

The first movable amount of the at least one floating stop may be determined by an amount of movement of the at least one floating stop rotating at least partially about the rotation axis from a first stop position, in which the at least one floating stop engages both the first stop surface and the first contact face, to an intermediate position, in which the at least one floating stop engages the second stop surface; and the second movable amount of the at least one floating stop may be determined by an amount of movement of the at least one floating stop rotating at least partially about the rotation axis from the intermediate position to a second stop position, in which the at least one floating stop engages both the second stop surface and the second contact face.

The second stop surface may be configured to move the at least one floating stop within the cavity from the intermediate position to the second stop position.

The first and second stop surfaces may be formed by opposite sides of at least one fixed stop radially outwardly protruding from an outer surface of the shaft, the at least one fixed stop being non-rotatable about the rotation axis.

The at least one floating stop may include a spherical ball.

The elongated cavity may be formed by radially inwardly projecting surfaces of the hub that at least partially enclose the at least one floating stop.

The radially inwardly projecting surfaces of the hub may form a radially inwardly projecting lug, and the first and second contact faces of the hub may form opposite end portion surfaces of the lug.

The first and second stop surfaces may radially overlap with the first and second contact faces of the hub, and radially overlap with the at least one floating stop; and the first and second contact faces may include respective openings for receiving the first and/or second stop surfaces, thereby enabling the first or second stop surface to move the at least one floating stop within the elongated cavity between the first and second contact faces.

The first and second stop surfaces may radially overlap with opposite first and second engagement surfaces of the at least one floating stop; and the first and second stop surfaces and the opposite first and second engagement surfaces of the at least one floating stop may lie in the same plane that is perpendicular to the rotation axis.

The first movable amount may be less than 360-degrees, and the second movable amount may be in a range from 1-degree to less than 180-degrees.

The at least 360-degrees rotation range may be less than 540-degrees.

The first and second stop surfaces may be formed by opposite sides of a fixed stop, and the shaft may include a plurality of receivers evenly spaced about the rotation axis of the shaft for receiving the fixed stop.

The shaft may have an axial hollow and a radial aperture and the cavity of the hub may be positioned to allow passage of electrical and communication lines through the axial hollow, through the radial aperture, and into a longitudinally extending cavity in the extension arm.

The hub of the extension arm may include upper and lower pivot bearings configured to pivotably engage the hub with the shaft, and a radial opening positioned axially between the upper and lower pivot bearings; and the cavity of the hub may be positioned to allow passage of the electrical and communication lines between the upper and lower pivot bearings, through the radial opening of the hub, and into the longitudinally extending cavity in the extension arm.

According to another aspect of the invention, a medical device support system includes a shaft, an extension arm, and at least one floating stop. The extension arm may have a support for a medical device. A hub at a proximal end of the extension arm may be mounted to the shaft for pivotable movement of the extension arm and the hub about a rotation axis of the shaft. The hub may include an elongated cavity having first and second contact faces. The at least one floating stop may be disposed in the cavity and be movable between the first and second contact faces. First and second stop surfaces may be fixed relative to the shaft and radially extend to overlap with a rotation path of the at least one floating stop. The hub may be pivotably mounted for a range of at least 360-degrees rotation about the rotation axis from a first stop position to a second stop position and vice versa, wherein at the first stop position, the first stop surface engages a first engagement surface of the at least one floating stop and an opposite second engagement surface of the at least one floating stop engages the first contact face of the cavity, thereby limiting further counterclockwise rotation of the hub about the rotation axis, and wherein at the second stop position, the second stop surface engages the second engagement surface of the at least one floating stop and the opposite first engagement surface of the at least one floating stop engages the second contact face of the cavity, thereby limiting further clockwise rotation of the hub about the rotation axis.

Embodiments of the invention may include one or more of the following additional features separately or in any combination.

The at least one floating stop may be configured to move with the hub about the rotation axis from the first stop position to an intermediate position between the first and second stop positions, wherein at the intermediate position the at least one floating stop engages with the second stop surface; and wherein the second stop surface is configured to move the at least one floating stop within the elongated cavity from the intermediate position to the second stop position.

According to another aspect of the invention, there is provided a method of rotating an extension arm about a shaft of a medical device support system, the extension arm having a support for a medical device and a hub at its proximal end mounted to the shaft for pivotable movement about a rotation axis of the shaft, the method including rotating the hub over a range of at least 360-degrees about the rotation axis, wherein the at least 360-degrees rotation range is based on a compound of movement over a first rotation range and movement over a second rotation range, wherein movement over the first rotation range includes moving at least one floating stop of the hub between first and second stop surfaces fixed relative to the shaft, and wherein movement over the second rotation range includes moving the at least one floating stop with the first or second stop surface between first and second contact faces of an elongated cavity of the hub.

The following description and the annexed drawings set forth certain illustrative embodiments of the invention. These embodiments are indicative, however, of but a few of the various ways in which the principles of the invention may be employed. Other objects, advantages and novel features according to aspects of the invention will become apparent from the following detailed description when considered in conjunction with the drawings.

BRIEF DESCRIPTION OF THE DRAWINGS

The annexed drawings, which are not necessarily to scale, show various aspects of the invention.

DETAILED DESCRIPTION

Figure 1:
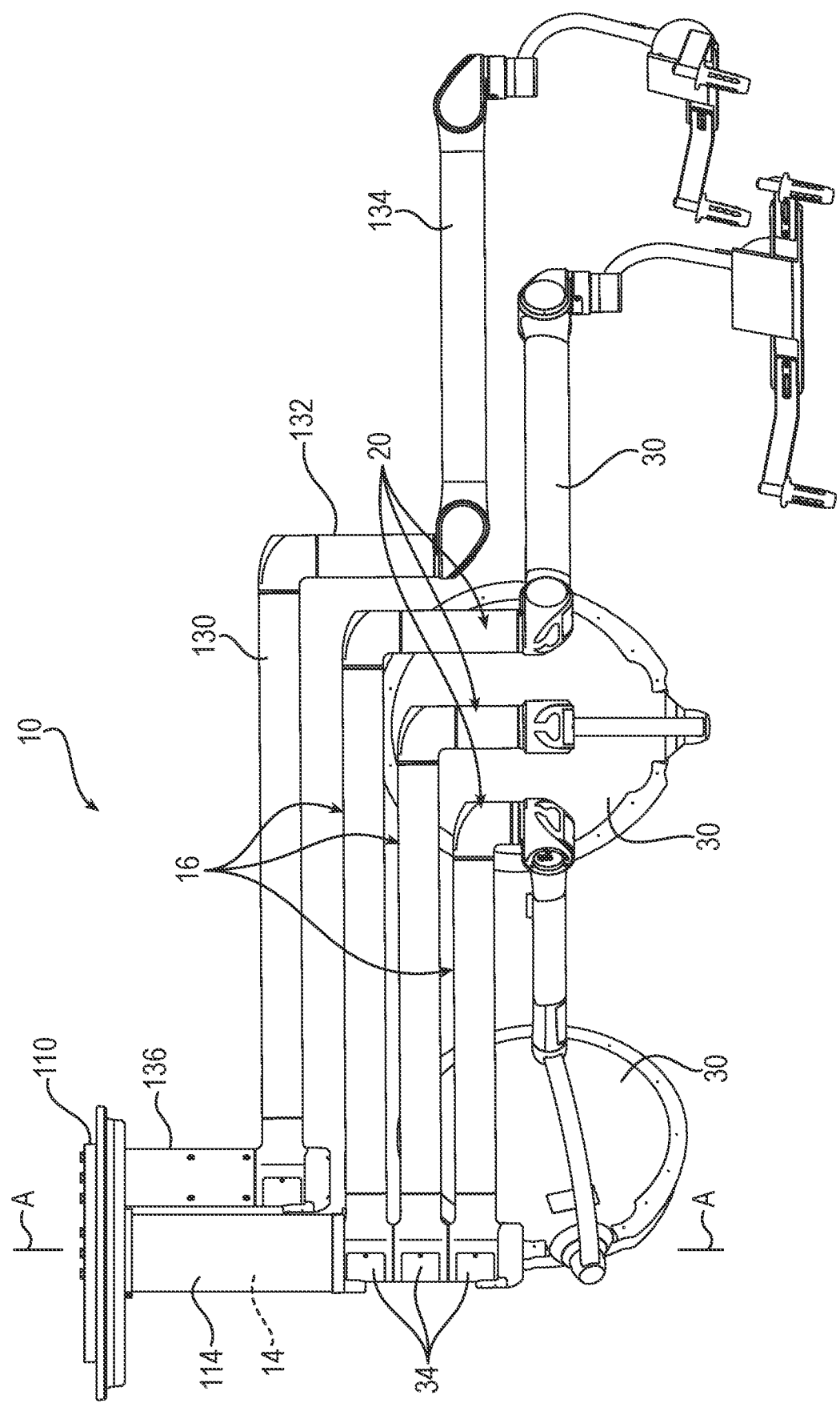
FIG. 1 is a front elevational view of an exemplary medical device support system in accordance with an embodiment of the invention.

While the present invention can take many different forms, for the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications of the described embodiments, and any further applications of the principles of the invention as described herein, are contemplated as would normally occur to one skilled in the art to which the invention relates.

Figure 2:
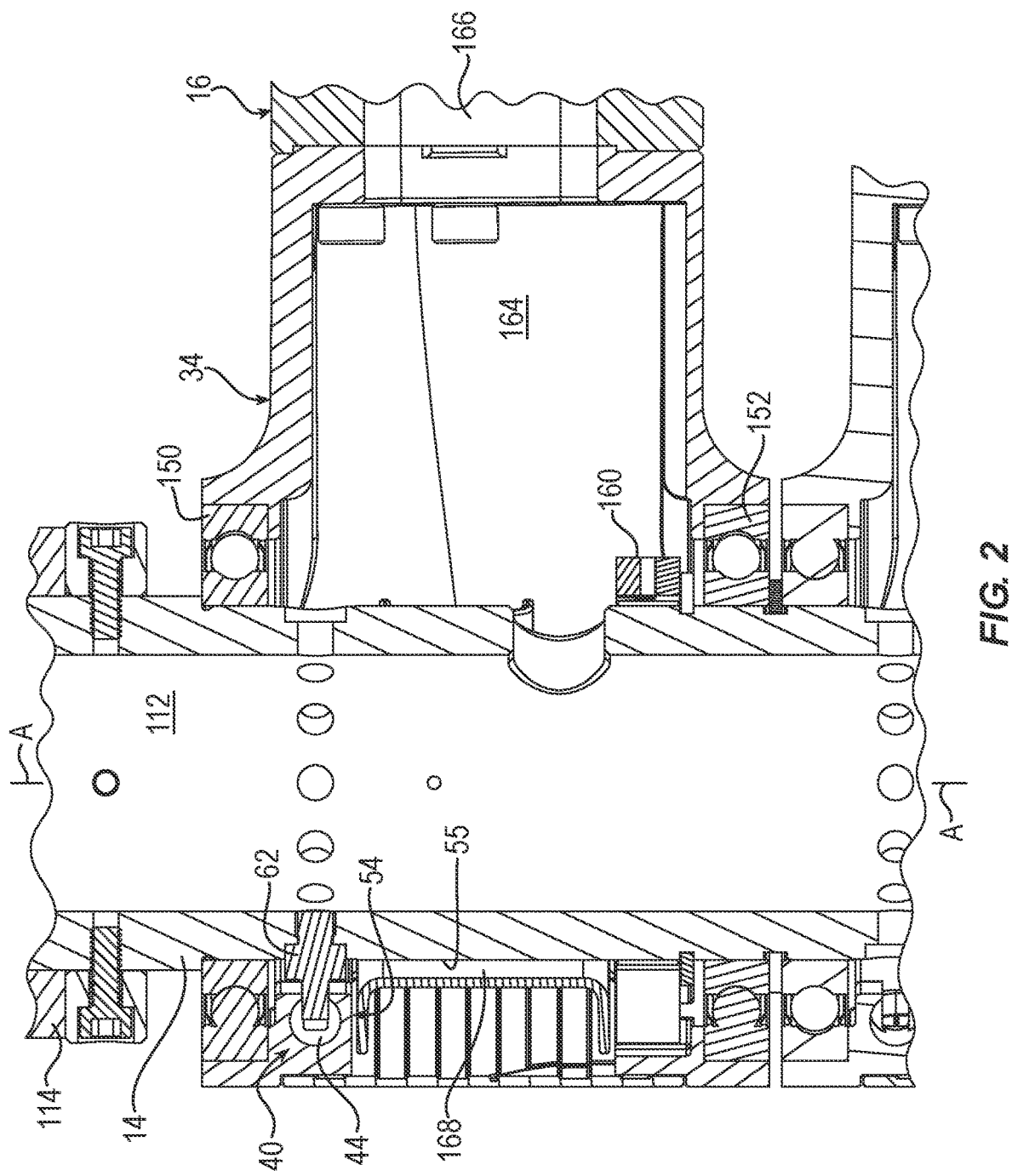
FIG. 2 is a cross section view of an exemplary shaft and exemplary extension arm hub connection of the FIG. 1 medical device support system, showing an exemplary rotational control mechanism in accordance with an embodiment of the invention.
Figure 4:
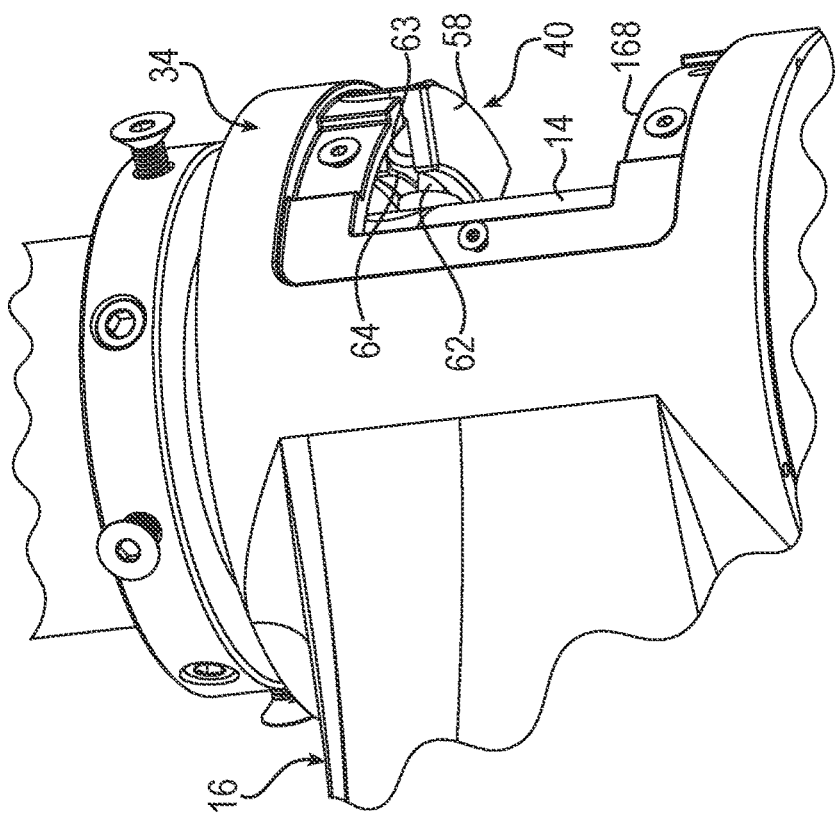
FIG. 4 is a bottom, left isometric view of the shaft and extension arm hub connection in FIG. 3.
Figure 3:
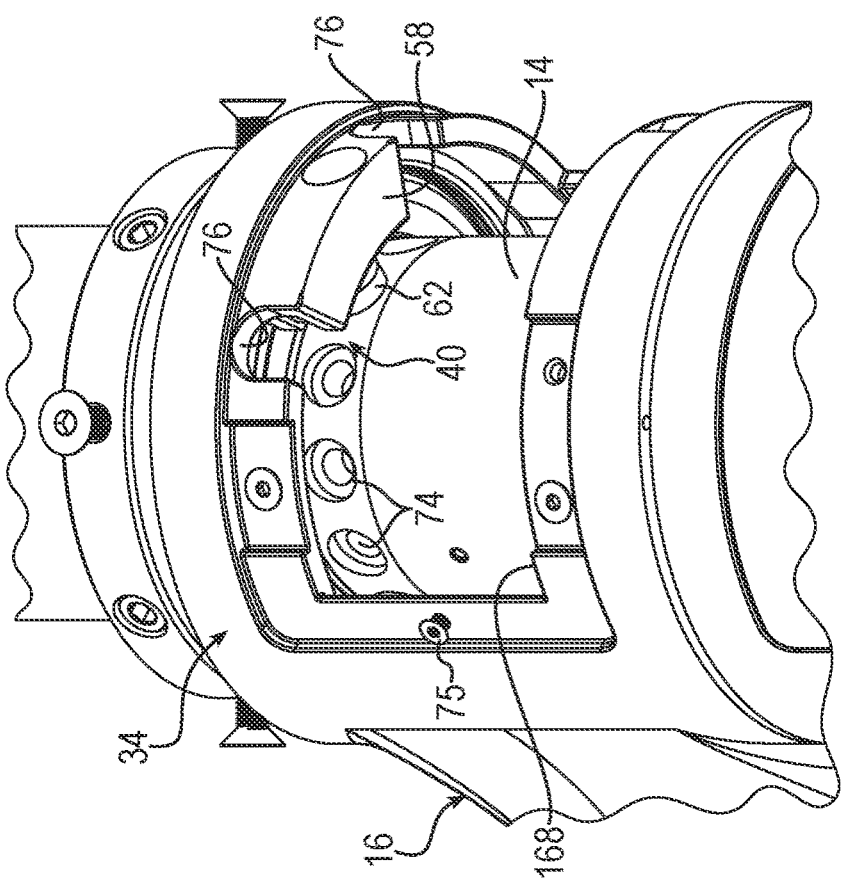
FIG. 3 is a bottom, front, left isometric view of the FIG. 2 shaft and extension arm hub connection, including a portion of the rotational control mechanism.
Figure 5:
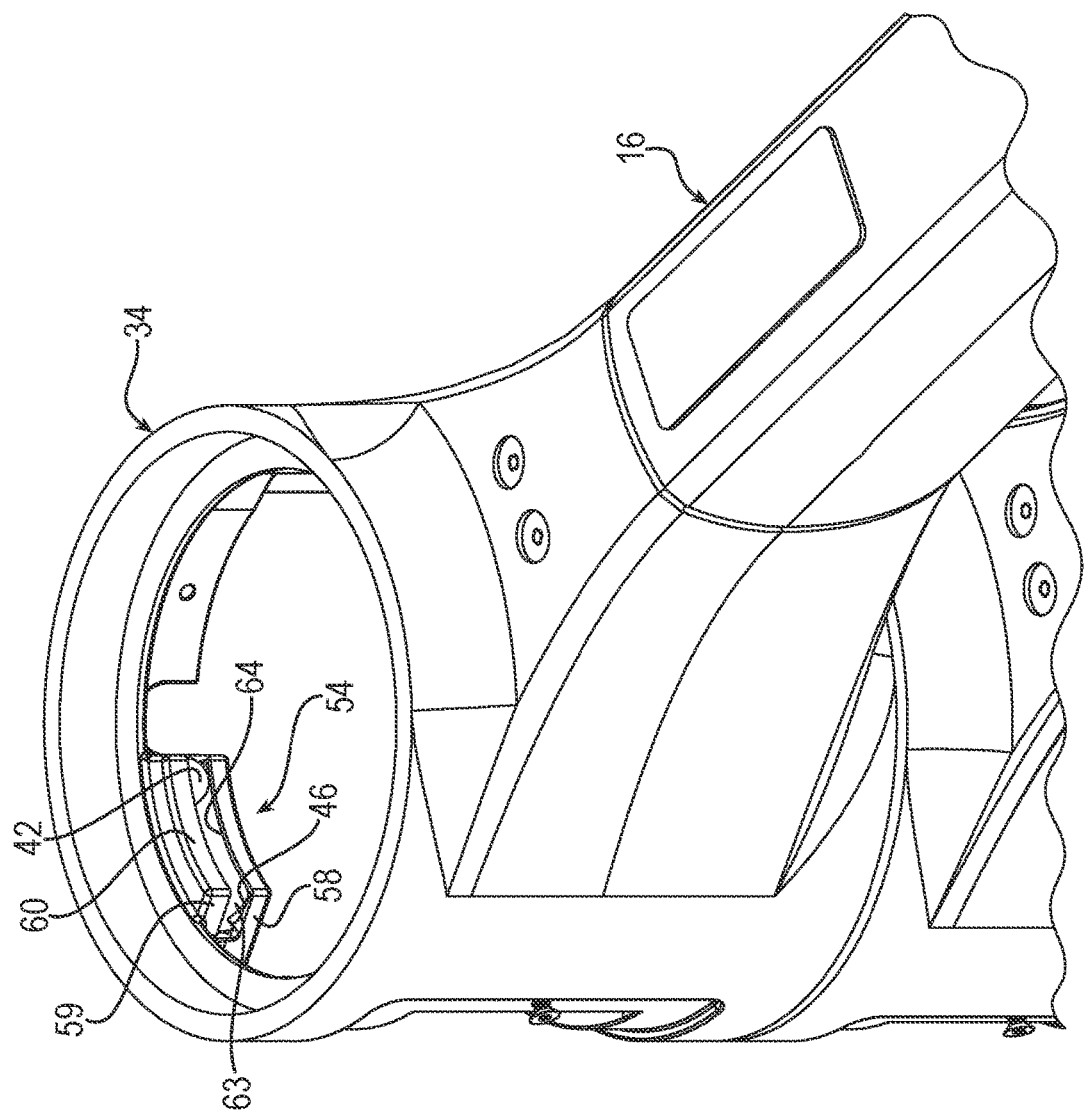
FIG. 5 is a top, rear, right isometric view of the FIG. 2 extension arm hub, including a portion of the rotational control mechanism, but shown without the shaft.
Figure 6:
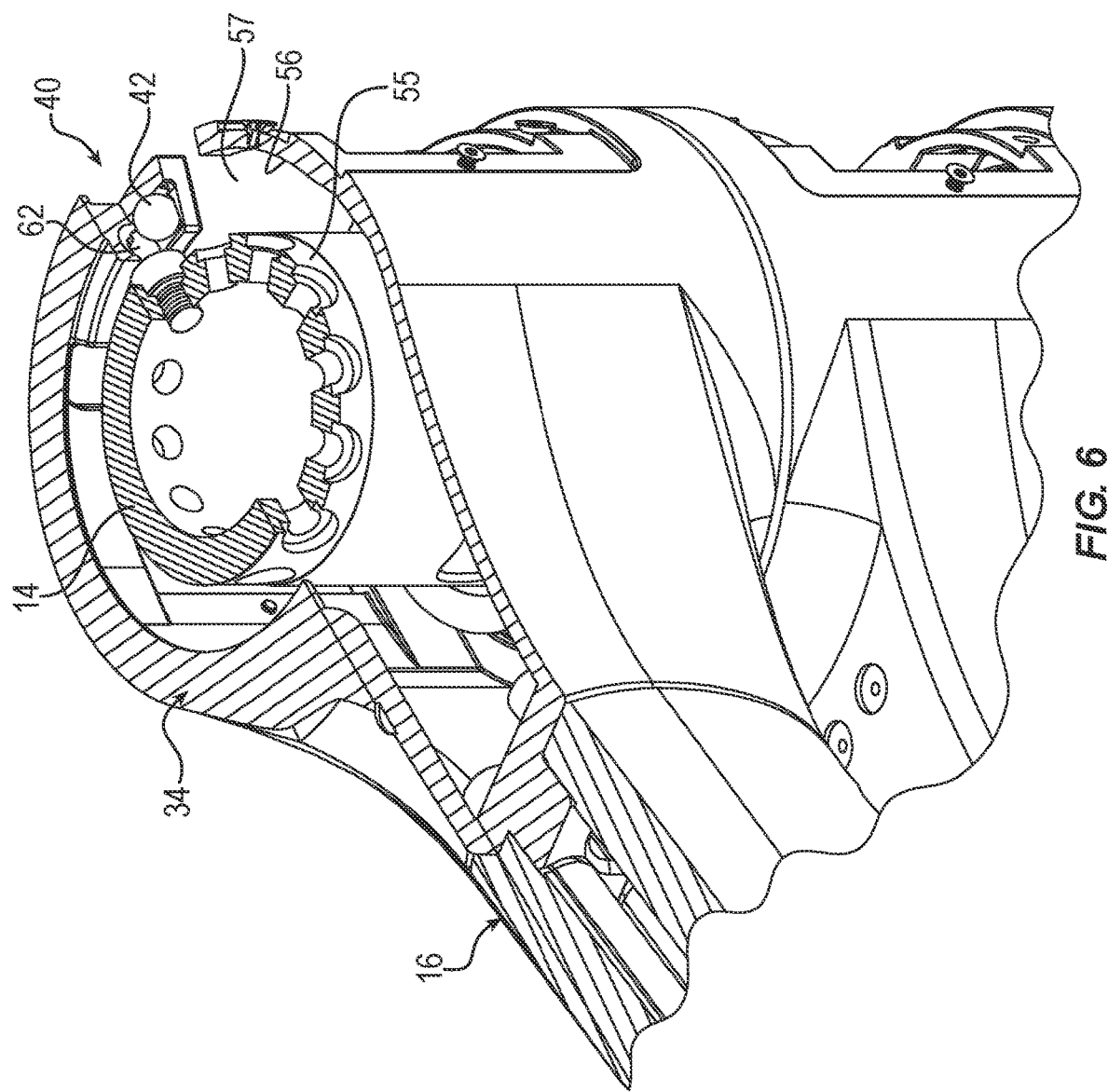
FIG. 6 is partial cross-section, partial quarter section, and top, rear, left isometric view of the FIG. 2 shaft and extension arm hub connection, including the rotational control mechanism.

Referring initially to FIGS. 1 and 2, an exemplary medical device support system 10 is shown. The medical device support system 10 generally includes a shaft 14, at least one extension arm 16 having a support 20 for a medical device 30, and a hub 34 at a proximal end of the extension arm 16 and mounted to the shaft 14 for pivotable movement about a rotation axis A-A of the shaft 14. The medical device support system 10 also includes an exemplary rotational control mechanism 40 integrated into the hub 34 and which cooperates with the shaft 14 to control an amount of rotation of the extension arm 16 about the shaft 14.

According to an aspect of the present invention, the exemplary rotational control mechanism 40 enables a range of at least 360° (360-degrees) rotation of the extension arm 16 about the rotation axis A-A of the shaft. More specifically, according to at least one aspect of the invention which is described in further detail below, the exemplary rotational control mechanism 40 described herein includes at least one floating stop movably disposed in an elongated cavity of the hub, and which interacts with first and second contact faces of the hub, and with first and second stop surfaces fixed relative to the shaft, for providing the range of at least 360-degrees rotation of the extension arm 16 about a rotation axis A-A of the shaft 14.

As shown in the illustrated embodiment, the medical device support system 10 may be a suspension type carrying support system for use in a hospital examination room, a clinic, a surgery room, an emergency room, among others. The shaft 14 extends along axis A-A, which also represents the rotation axis A-A of the shaft 14 about which the extension arm 16 pivots. The shaft 14 may be fixed to a ceiling support 110 to remain stationary relative to the ceiling. It will be appreciated, of course, that the medical device support system 10 may have any suitable suspension or carrying structure and that the shaft 14 may be attached to a ceiling as shown, or to a wall, floor, movable cart, or a combination of the foregoing.

In exemplary embodiments, the shaft 14 of the medical device support system 10 has a cylindrical shape in axial cross section and defines an axial hollow 112 therein, and extends vertically downward from the ceiling support 110. A column section 114 surrounds an upper portion of the shaft 14. The axial hollow 112 and the column section 114 house upper portions of accessory and service lines such as power cables for surgical lights and other power requirements, control wiring for control electronics, optical fibers for data communication, and/or tubing for irrigation, suction, etc. A plurality of extension arms 16, such as three in the illustrative embodiment, are mounted for rotatable movement to the shaft 14 and extend laterally outward from the shaft 14. In the FIG. 1 embodiment, the extension arms 16 extend horizontally, or perpendicularly, relative to the shaft 14. An additional extension arm 130, support arm 132, and medical device 134 may be pivotably mounted to a separate central shaft 136 radially offset from the central shaft 14.

As shown, the hub 34 is located at the proximal end of the extension arm 16 and aids in the pivotable movement of the extension arm 16 about the shaft 14. The hub 34 may be unitary with the extension arm, or may attached to the proximal end of the extension arm 16 in any suitable manner. Each extension arm hub 34 may include upper and lower bearing mounts 150, 152 (as shown in FIG. 2, for example) that house respective upper and lower pivot bearings mounted to the shaft 14. The bearing mounts 150, 152 enable rotational movement of the extension arm 16 and hub 34. Any suitable pivot bearings may be used to enable the relative rotational movement between the extension arm 16 and the shaft 14, including for example ball bearings, sleeve bearings, bushings, rotary joints, swivel joints and/or the like.

A brake assembly 160 may be secured in the hub 34 for rotation therewith to selectively increase and decrease a frictional braking force to the shaft 14. In the illustrative embodiment, the brake assembly 160 is positioned above the lower bearing mount 152. Each hub 34 also may provide a radial opening 164, which may be positioned axially between the upper and lower pivot bearings 150, 152, for routing accessory and service lines from the axial hollow 112 and/or the upper column section 114 to a longitudinally extending cavity 166 of the extension arm 16, and/or vice versa. Each hub 34 is also provided with an access opening 168 to enable access to the shaft 14, the rotational control mechanism 40, the upper and lower pivot bearings 150, 152, the brake assembly 160, accessory and service lines, and/or other components within the hub 34. A suitable brake assembly 160 and access opening 168 for the illustrative embodiment are described in U.S. patent application Ser.

Nos. 16/517,703; 16/517,704; 16/517,707; and 16/517,708, which are incorporated by reference for all purposes as if fully set forth herein.

Referring now particularly to FIGS. 2-9, the exemplary rotational control mechanism 40 will now be described in further detail. Generally, the rotational control mechanism 40 is made up of a combination of contact faces, or surfaces, including those from the hub 34 and the shaft 14, which interact with at least one free floating member 42 to control the amount of rotation of the extension arm 16 about the rotation axis A-A of the shaft 14. The rotational control mechanism 40 enables the range of at least 360-degrees of rotation of the extension arm 16 about the rotation axis A-A of the shaft 14. More specifically, according to an aspect, the exemplary rotational control mechanism 40 includes the at least one floating member 42 in the form of a floating stop (also referred to with 42) that is movably disposed in a cavity 44 of the hub 34 to interact with first and second contact faces 46, 48 of the hub 34, and also which is configured to interact with first and second stop surfaces 50, 52 fixed relative to the shaft 14 for providing the range of at least 360-degrees rotation.

The at least 360-degrees rotation range of the extension arm 16 about the shaft 14 may be based upon a compound of ranges depending on the movement of the floating stop 42, and which contact faces 46, 48 or stop surfaces 50, 52 engage the floating stop 42, as will be described in further detail below. The compound of ranges includes at least a first rotation range and a second rotation range. In exemplary embodiments, the first rotation range is defined by a first movable amount of the at least one floating stop 42 between the first and second stop surfaces 50, 52 fixed relative to the shaft 14, and the second rotation range is defined by a second movable amount of the at least one floating stop 42 between the first and second contact faces 46, 48 in the cavity 44 of the hub 34.

The cavity 44 of the hub 34 containing the at least one floating stop 42 may be formed by any suitable surface or surfaces of the hub 34 that are configured to movably support and contain the floating stop 42, and which such surface(s) are configured to co-rotate along with the remainder of the hub 34. For example, the cavity 44 may be formed by at least one radially projecting surface of the hub 34, such as a shelf or rim, that supports the floating stop 42 during movement thereof. In the illustrated embodiment, the cavity 44 is formed by a radially projecting segment, or lug 54, of the hub 34. In exemplary embodiments, the floating stop 42 is configured to move within the cavity 44 along a circumferential path about the axis A-A between the first and second contact faces 46, 48 of the hub 34 (as described in further detail below). As such, the cavity 44 containing the floating stop 42 may be configured as an elongated circumferential channel that guides the floating stop 42 along its circumferential path.

As shown, the cavity 44 of the hub 34 containing the at least one floating stop 42 may be located in an annular region between a radially outer surface 55 of the shaft 14 and a radially inner surface of the hub 34. In the illustrated embodiment, for example, a radially inner surface 56 of the hub 34 is radially outwardly spaced from the radially outer surface 55 of the shaft 14 to form an annular gap 57. The cavity 44 is formed by the lug 54 (or other suitable support) of the hub 34 that projects radially inwardly from the radially inner surface 56 of the hub 34 into the annular gap 57. As shown, the lug 54 forming the cavity 44 contains the floating stop 42 with a lower radially projecting wall 58 and an upper radially projecting wall 59, each of which include corresponding axially extending surfaces that together form a circumferential wall 60 that at least partially encloses the cavity 44 and contains the floating stop 42. In exemplary embodiments, the circumferential wall 60 of the lug 54 is radially spaced apart from the outer surface 55 of the shaft 14 to prevent or minimize contact and thus minimize friction.

To restrict rotational movement of the floating stop 42 about the axis A-A, and thereby control the rotation of the extension arm 16 and hub 34 relative to the shaft 14, the hub 34 provides the first and second contact faces 46, 48 (also referred to as stop surfaces) on opposite sides of the hub cavity 44. The contact faces 46, 48 are configured to engage with the floating stop 42 when the extension arm 16 and hub 34 are pivotably rotated about the shaft 14 between opposite first (FIG. 7) and second (FIG. 9) stop positions, which are at least 360-degrees apart, as described in further detail below. As shown in the illustrated embodiment, the first and second contact faces 46, 48 are angularly (circumferentially) spaced apart from each other along the rotational path of the floating stop 42 to define opposite ends of the lug 54 of the hub 34. The contact faces 46, 48 of the hub 34 may be provided in any suitable manner, such as being integral and unitary with the lug 54 and/or other portions of the hub 34, as shown; or may be provided as discrete members, such as pins, screws, or the like, which are coupled to the hub 34.

As is apparent in the illustrated embodiment, the angular (circumferential) spacing between the first and second contact faces 46, 48 of the hub 34 may be used to set the rotational limits of the extension arm 16 and hub 34 relative to the shaft 14 to 360-degrees, or may be used to set the rotational limits of the extension arm 16 and hub 34 relative to the shaft beyond 360-degrees. Such angular spacing and rotational control also may be determined, at least in part, by the angular span (circumferential distance) between opposite sides of the at least one floating stop 42 (or multiple floating stops) and the angular span (circumferential distance) between the opposite first and second contact surfaces 50, 52 that are fixed relative to the shaft 14. Generally, the greater the angular span between contact faces 46, 48 of the hub 34, the greater the amount of rotation beyond 360-degrees.

The floating stop 42 may be any suitable member that is free to rotate about the axis A-A relative to each of the hub 34 and the shaft 14, and which is permitted to interact with the first and second contact faces 46, 48 of the hub 34, and also interact with the relatively fixed first and second stop surfaces 50, 52 (fixed relative to the shaft 14), to thereby control rotational movement of the hub 34 relative to the shaft 14. Such interaction of the floating member 42 with the contact faces 46, 48 and stop surfaces 50, 52 also enables the at least 360-degrees of rotation of the hub 34 about the shaft 14, as described in further detail below.

Generally, the floating stop 42 is configured to withstand the forces (e.g., compressive forces) imparted upon it during engagement with the respective contact faces 46, 48 and/or stop surfaces 50, 52. To withstand such forces without permanent deformation, the floating stop 42 may be made of a suitable rigid material, such as a stainless steel, or rigid plastic. To minimize stress risers on the floating stop 42, the contact faces 46, 48, and/or the stop surfaces 50, 52, such engagement interfaces may be configured in a complimentary manner to each other to enhance contact area. In some embodiments, the floating stop 42 (or at least one of the floating stops when multiple are used) may provide damping characteristics to the movement between stop positions. In such embodiments, the at least one floating stop 42 may be made of a suitable elastomer, for example. In exemplary embodiments, the floating stop 42 also is configured to slide along the surfaces of the hub 34 (e.g., lug 54) forming the cavity 44 with minimal friction and wear. Suitable anti-friction or slip-coatings may be provided on such surfaces of the hub 34 and/or floating stop 42 to reduce friction and wear.

Figure 7:
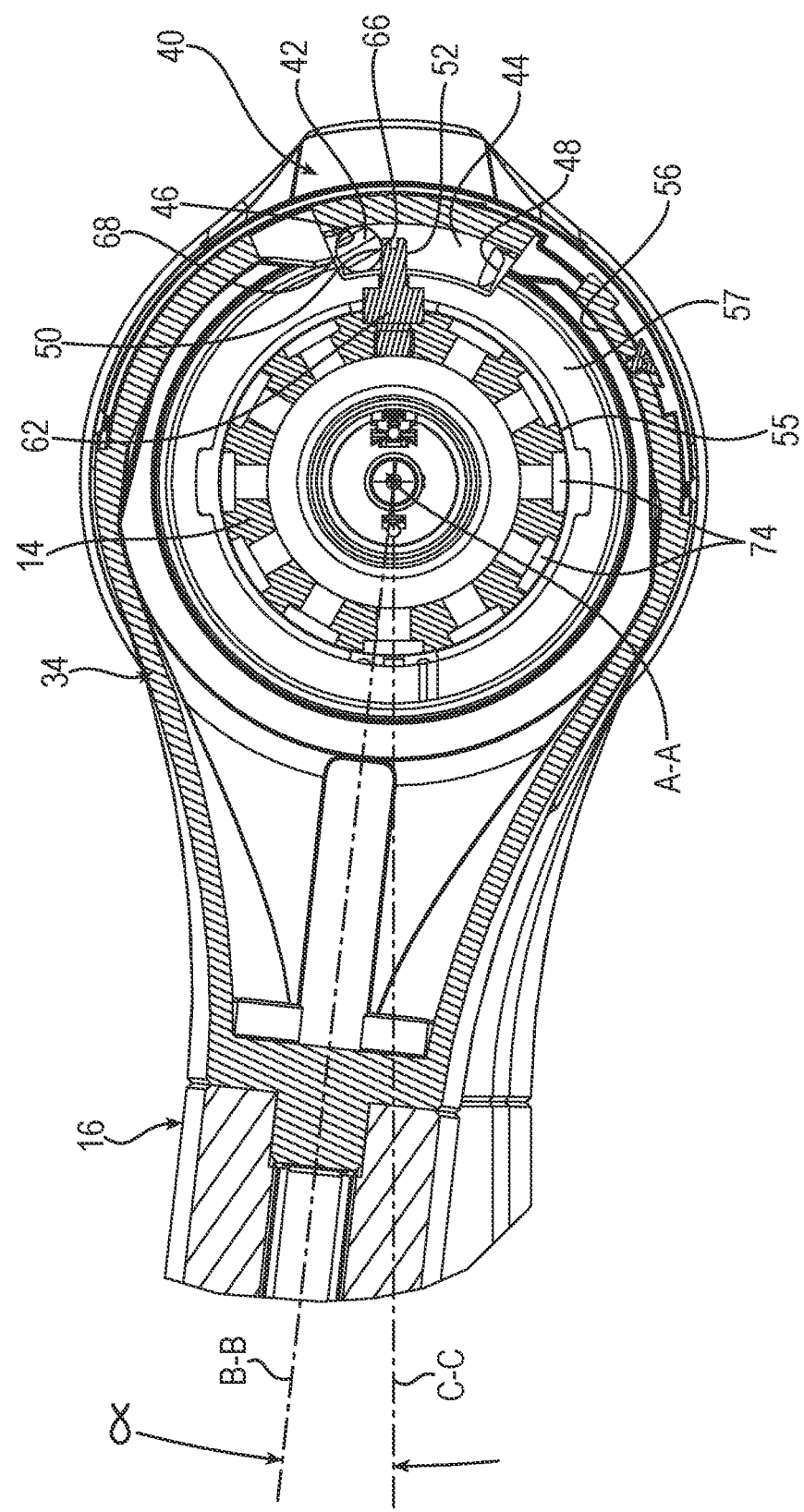
FIG. 7 shows a top cross section view of the rotational control mechanism of the medical device support system of FIG. 1, showing a maximum clockwise position of the rotational control mechanism.
Figure 8:
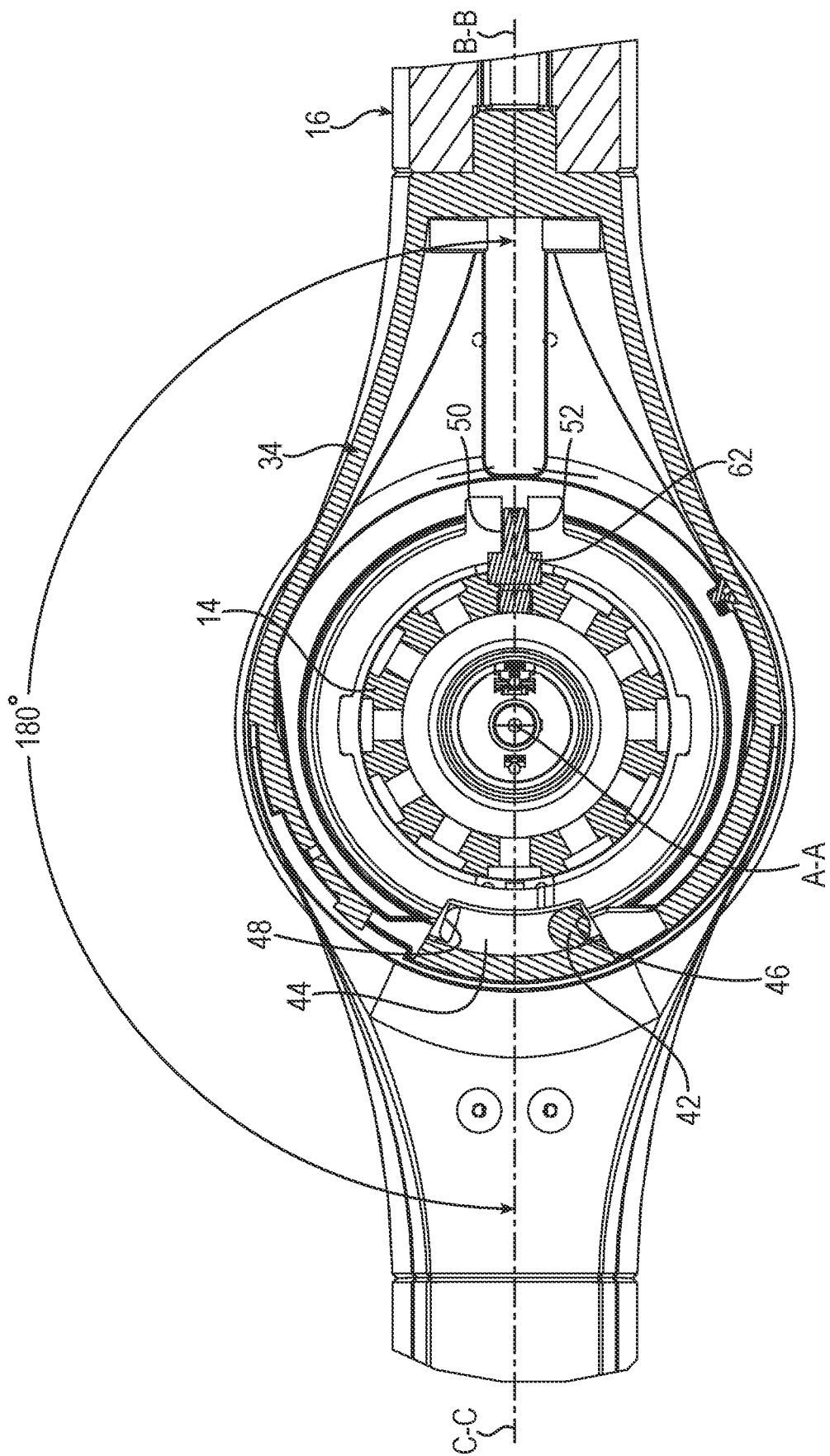
FIG. 8 shows a top cross section view of the rotational control mechanism of the medical device support system of FIG. 1, showing an intermediate rotation position of the rotational control mechanism.

As shown in the illustrated embodiment, to further enhance movability of the floating stop 42 without binding, and to minimize friction and wear, the at least one floating stop 42 is configured as a spherical ball bearing. The surface(s) forming the elongated cavity 44 also may be formed as curved bearing race(s) for providing a suitable rolling interface with the ball bearing (also referred to with 42). As shown in the illustrated embodiment, for example, the internal surfaces of the lug 54 forming the cavity 44 are formed in a curved shape that is complimentary to the spherical shape of the ball bearing 42. The bearing race of the lug 54 is formed in a complimentary arcuate shape that enables the ball bearing 42 to move along its rotational, or circumferential, path to engage the first and second contact faces 46, 48 on the opposite sides of the cavity 44. As best shown in FIGS. 7-8, for example, the first and second contact faces 46, 48 of the hub 34 also may be formed in a complimentary shape to the shape of the spherical ball bearing 42 to enhance contact area when the ball bearing 42 interfaces against the contact faces 46, 48.

The first and second stop surfaces 50, 52 fixed relative to the shaft 14 may be provided as any suitable structure (or combination of structures) configured to interface with the at least one floating stop 42 and thereby provide interaction with the contact faces 46, 48 of the hub 34 to control rotation of the extension arm 16 relative to the shaft 14. In exemplary embodiments, the first and second stop surfaces 50, 52 are fixed in position relative to the radially outer surface 55 of the shaft 14 (i.e., are non-rotatable about the axis A-A). In the illustrated embodiment, the first and second stop surfaces 50, 52 are formed by fixed stop 62 operatively coupled to the shaft 14, such that the first and second stop surfaces 50, 52 form opposite sides of the fixed stop 62. As shown, the fixed stop 62 may be a single fixed stop. The fixed stop 62 may be in the form of a pin, bar, rod, roller, or other protuberance coupled to the shaft 14 and which is non-rotatable about the axis A-A. It is understood that more than one such fixed stop 62 (e.g., pin), or other suitable structure (e.g., protuberance or recess), may be provided to form the first and second stop surfaces 50, 52, as would be understood by those having ordinary skill in the art.

To provide engagement with the floating stop 42 when the hub 34 is rotated about the shaft 14, the first and second stop surfaces 50, 52 (e.g., the fixed stop 62) are configured to radially overlap with the rotational path of the floating stop 42. For example, in the illustrated embodiment where the hub 34 is disposed radially outwardly of the shaft 14, the first and second stop surfaces 50, 52 radially outwardly protrude relative to the outer surface 55 of the shaft 14 to interact with the floating stop 42 disposed in the cavity 44 of the hub 34. As shown, the fixed stop 62 having the stop surfaces 50, 52 may protrude radially outwardly relative to the outer surface 55 of the shaft 14 to extend radially across at least a portion of the annular gap 57 to a position at which a first engagement surface 66 of the floating stop 42 can engage the first stop surface 50 of the fixed stop 62, and a second (opposite) engagement surface 68 of the floating stop 42 can engage the second stop surface 52 of the fixed stop 62, as will be described in greater detail below. Also as shown (such as in FIG. 5), the lug 54 (or other hub segment) containing the floating stop 42 may include suitable openings 63 in the contact faces 46, 48, and includes a slot 64 along the circumferential wall 60, to enable the fixed stop 62 (e.g., pin) to be received within the cavity 44 to engage the floating stop 42 and move circumferentially within the cavity 44. In this manner, and as described in further detail below, the fixed stop 62 (e.g., pin) is received into the opening of the cavity 44 to enable engagement with, and movement of, the floating stop 42 from one rotational end position at the first contact face 46 to the opposite rotational end at the second contact face 48, thereby providing rotational control and enabling the at least 360-degrees of rotation. It is understood that although shown and described as the fixed stop 62 extending radially across the annular gap 57 to engage the floating stop 42, alternatively or additionally the floating stop 42 could include a radially inwardly protruding portion that extends radially across at least a portion, or the entirety, of the annular gap 57 to contact the first and second fixed stop surfaces 50, 52 (fixed relative to the shaft 14), as would be understood by those having ordinary skill in the art.

As shown in the illustrated embodiment, the fixed stop 62 protruding radially outwardly relative to the shaft 14 and the floating stop 42 protruding radially inwardly relative to the wall of the hub 34 lie in the same horizontal plane that is perpendicular to the rotation axis A-A. Also shown in the illustrated embodiment, the radially inwardly protruding portion of the hub 34 (e.g., lug 54) and the floating stop 42 lie in the same horizontal (rotational) plane with each other, and lie in the same plane with the fixed stop 62, which said plane is perpendicular to the rotation axis A-A. In this way, the rotational control mechanism 40 embodies fewer components and a smaller volumetric footprint than heretofore attained, and simplifies and adds efficiency to the factory assembly and field service of the medical device support system 10. Of course, the invention need not be limited as such and other embodiments are contemplated. For example, the radially outward protruding fixed stop 62 may be located in a plane axially above or axially below the plane in which the floating stop 42 and the elongated cavity 44 lie. In another example, the radially outward protruding fixed stop 62 may be located in a plane axially above or axially below the plane in which the floating stop 42 lies, and the elongated cavity 44 may have an axial height such that the radially outward protruding fixed stop 62 and the floating stop 42, although themselves in different planes, both lie in the axial height plane of the elongated cavity 44.

In the illustrative rotational control mechanism 40, there is only a single cavity 44 in a hub projection (e.g., lug 54) holding a single floating stop 42 (e.g., ball bearing) configured to interact with a single fixed stop 62 (e.g., pin). It will be appreciated, however, that more than one elongated cavity 44, more than one floating stop 42 and/or more than one fixed stop 62 may be suitable for the rotational control mechanism 40. In other embodiments, there may be, two, four, etc. such respective components. It is furthermore noted that the number of elongated cavities 44 need not be the same as the number of radially outwardly protruding fixed stops 62.

Figure 9:
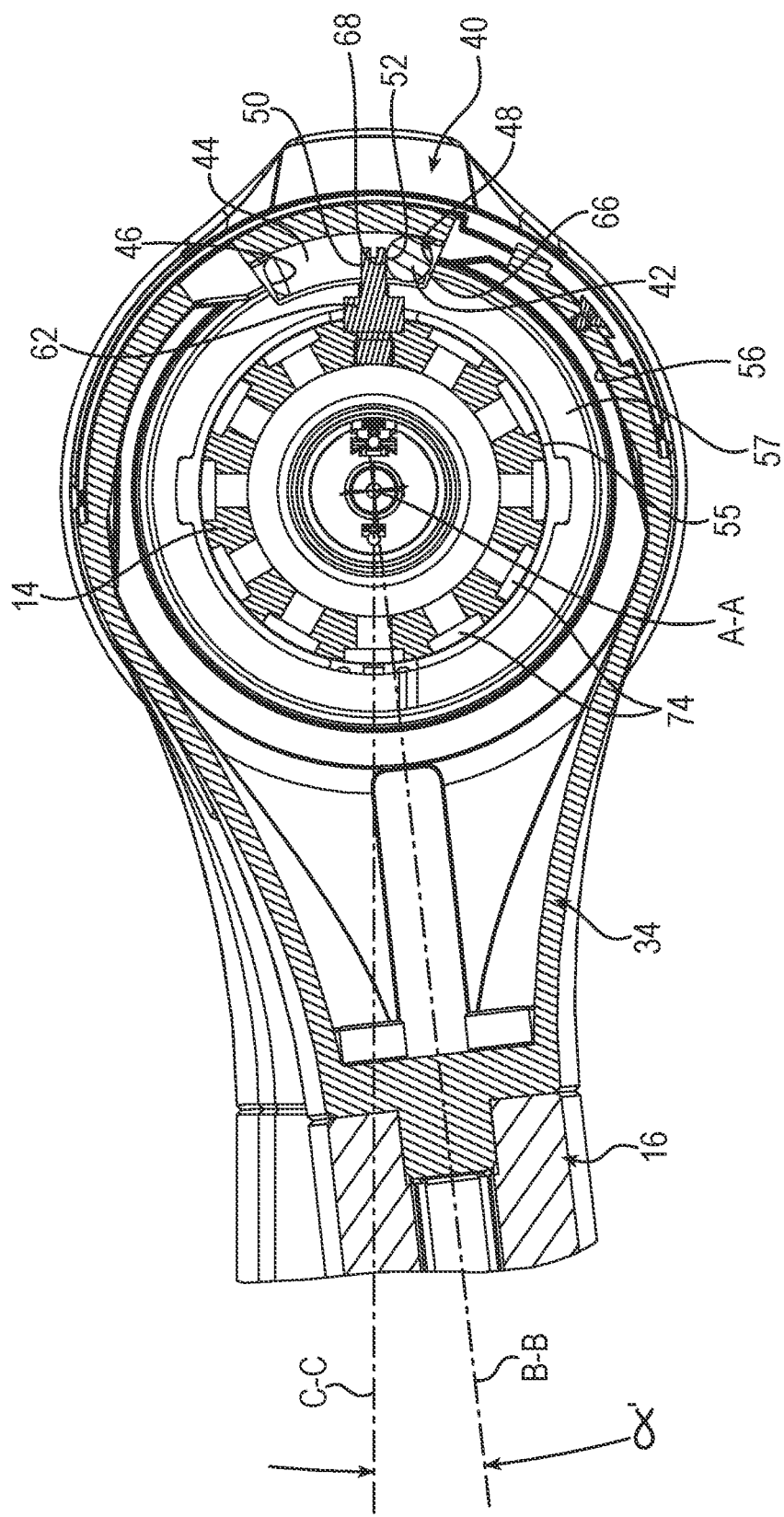
FIG. 9 shows a top cross section view of the rotational control mechanism of the medical device support system of FIG. 1, showing a maximum counterclockwise position of the rotational control mechanism, where the rotation is at least 360-degrees rotation from that shown in FIG. 7.

Referring now more particularly to FIGS. 7-9, an exemplary operation of the rotational control mechanism 40 will now be described in further detail. As discussed above, the rotational control mechanism 40 may enable the at least 360-degree rotation range based on a compound of a first rotation range and a second rotation range. In the illustrated embodiment, the first rotation range is determined by the at least one floating stop 42 being movable by a first amount between the first and second stop surfaces 50, 52 fixed relative to the shaft 14 (e.g., opposite sides of the fixed stop 62, or pin 62) due to rotational movement of the hub 34 relative to the shaft 14. In the illustrated embodiment, the second rotation range is determined by the at least one floating stop 42 being movable by a second amount within the elongated cavity 44 between the first and second contact faces 46, 48 of the hub 34 due to forces imparted by engagement with the stop surface(s) 50, 52 (e.g., sides of the pin 62). In this manner, the hub 34 is pivotably mounted for a range of at least 360-degrees rotation about the rotation axis A-A from a first stop position to a second stop position and vice versa.

The exemplary operation will be shown and described in even further detail, starting with reference to FIG. 7 and comparing this to FIG. 8. In FIG. 7, the illustrative rotational control mechanism 40 is shown in its first stop position. As shown, in the first stop position, the first stop surface 50 (e.g., first side of the pin 62) engages a first engagement surface 66 of the floating stop 42. The floating stop 42 is sandwiched between the first stop surface 50 (e.g., pin) and the first contact face 46 of the hub 34, such that a second (opposite) engagement surface 68 of the floating stop 42 engages the first contact face 46. As is apparent in the illustrated state of FIG. 7, the ability to further rotate the hub 34 clockwise about the axis A-A is restricted. However, in the illustrated state of FIG. 7, the hub 34 is free to rotate about the axis A-A in a counterclockwise direction, as shown with comparative reference to FIG. 8.

FIG. 8 shows an intermediate rotational state in which the hub 34 has been rotated counterclockwise about the axis A-A of the shaft 14 by about 180-degrees relative to the first stop position shown in FIG. 7. As shown, assuming that the floating stop 42 remains idle or stationary with respect to rotation of the hub 34, the floating stop 42 is co-rotated along with the hub 34 to the intermediate position. In the illustrated state, for example, the floating stop 42 is less than 180-degrees from contacting the second stop surface 52 (e.g., second side of pin 62). As the hub 34 continues its rotation in the counterclockwise direction, the floating stop 42 will continue to be carried along with the hub 34 in the counterclockwise direction. It is understood that by virtue of forces (e.g., inertia) and/or friction coefficient, the floating stop 42 may move or shift within the cavity 44 during rotation of the hub 34, such that the floating stop 42 (e.g., ball) does not remain exactly in the same position during rotational movement of the hub 34. It also is understood that the hub 34 may be rotated back in the clockwise direction from the intermediate position, or any other position between its first and second stop positions, as may be desired during use of the medical device.

Although not expressly shown in the illustrated states, it is understood by comparing the intermediate position in FIG. 8 to the second stop position in FIG. 9, that the first rotation range of the rotational control mechanism is achieved when the floating stop 42 moves about the axis A-A with the hub 34 from the first stop surface 50 (e.g., the first side of the pin 62) to engagement with the second stop surface 52 (e.g., the second, opposite side of the pin 62). In the illustration, it is assumed that the second engagement surface 68 of the floating stop 42 remains in its position relative to the hub 34 during rotation, i.e., in engagement with the first contact face 46 of the hub 34.

With the foregoing intermediate state in mind, and with comparative reference to FIG. 9, in the illustrated embodiment the second rotation range begins when the second engagement surface 68 of the floating stop 42 engages with the second stop surface 52 (e.g., second side of pin 62) and ends when the opposite engagement surface 66 of the floating stop 42 engages with the second contact face 48 of the hub 34. Within this second rotation range, the fixed stop 62 (e.g., pin) is configured to enter into the cavity 44 via the opening 63 in the first contact face 46 of the hub 34, and engage with and apply force to move the floating stop 42 within the cavity 44. Because the floating stop 42 may be unconstrained from movement in its circumferential path in the cavity 42, the fixed stop 62 (e.g., pin) moves along the slot 64 in the circumferential wall 60, and continues to apply force to move the floating stop 42 until the floating stop 42 engages the second contact face 48 of the hub 34. At the second stop position (shown in FIG. 9), the at least one floating stop 42 is sandwiched between the second stop surface 52 (e.g., pin 62) and the second contact face 48 of the hub 34, restricting further counterclockwise rotation of the hub 34 relative to the axis.

It is apparent from the foregoing exemplary operation that the same process, but in reverse, can be applied for clockwise rotation of the arm 16 and hub 34 relative to the shaft 14 and axis A-A to provide corresponding first and second rotation ranges to achieve the at least 360-degrees in the opposite direction.

As will be appreciated, in the illustrated embodiment where the floating stop 42 is configured as a ball 42, for example, the second engagement surface 68 of the ball 42 that engages with the first contact face 46 of the hub 34 may roll as the ball 42 moves within the cavity 44, such that this same engagement surface 68 may engage with the second contact face 48 of the hub 34. Thus, reference to the "first" and "second" engagement surfaces 66, 68 of the floating stop 42 refers to those engagement surfaces in a state when interfacing against an opposing surface, understanding that it can be the same surface of the floating stop 42 making such contact by virtue of the movement (e.g., rolling) in the cavity 44. Similarly, if the fixed stop 62 is configured as a roller that rotates about its own axis but does not rotate about the axis A-A, then such roller may have first and second stop surfaces 50, 52 in engagement with the floating stop 42, which these "first" and "second" stop surfaces may be the same depending on the rolling position of the roller (fixed stop 62).

Also as will be appreciated, in operation, the first and second rotation ranges might not be completed in serial fashion but rather may be completed at least partially in parallel fashion. For example, it will be appreciated that the first movement amount of the floating stop 42 between the first and second stop surfaces 50, 52 (e.g., opposite sides of the pin 62), and the second movement amount of the floating stop 42 between the first and second contact faces 46, 48 on opposite sides of the cavity 44, may vary depending on the forces and/or friction between the respective rotating and/or sliding surfaces of these components. Thus, while FIG. 7 shows the start of the first and second rotation ranges, and FIG. 9 shows the completion of the first and second rotation ranges, what occurs between the start and completion of the first and second rotation ranges may depend on the friction and/or forces (e.g., inertial forces) between the rotating and/or sliding surfaces.

It will be appreciated that the rotational control mechanism 40 can provide a rotation range greater than 360-degrees, or a rotation range equal to 360-degrees, or even a rotation range less than 360-degrees, by adjusting any of its components, for example the width (angular span) of the elongated cavity 44, and more particularly the width (angular span) between contact faces 46, 48; the width (angular span) between the first and second stop surfaces 50, 52 (e.g., opposite faces of the at least one fixed stop 62); and/or the width (angular span) between the opposite engagement surfaces 66, 68 of the floating stop 42.

In the illustrated embodiment, for example, the angular span between the first and second contact faces 46, 48 of the hub defining the elongated cavity 44 is about 45-degrees. The floating stop 42 (e.g., ball) has an angular span of about 13-degrees. The fixed stop 62 has an angular span of about 5-degrees. Thus, and assuming a negligible thickness at the opposite ends of the cavity 44 at the first and second contact faces 46, 48, the first rotation range is about 342-degrees (360 minus 13 minus 5), and the second rotation range (e.g., from the floating stop 42 first contacting the fixed stop 62 to then engaging the second contact face 48 of the hub 34) is about 32-degrees (45 minus 13). An example of the beginning of the first and second rotation ranges is shown in FIG. 7 and the end of the first and second rotation ranges is shown in FIG. 9. As shown in FIG. 7, a transverse axis B-B of the extension arm 16 perpendicular to the rotation axis A-A is at a first angular position with an angular offset α relative to a transverse axis C-C of the fixed stop 62 (e.g., pin), which this angle α is about 7-degrees clockwise from the transverse axis C-C in the illustrated embodiment. Comparing this to FIG. 9, where the extension arm 16 and hub 34 have rotated about the shaft 14 and axis A-A in a counterclockwise direction (that is, the extension arm 16 and hub 34 have rotated the first and second rotation ranges), the extension arm 16 (axis B-B) rotates counterclockwise from the angular position of FIG. 7 (that is, the position that is 7-degrees clockwise from the transverse axis C-C of the fixed stop 62) toward the transverse axis C-C, then 360-degrees, and then beyond the transverse axis C-C of the fixed stop 62 to a second angular position where the transverse axis B-B of the extension arm 16 is at an angular offset α' relative to the transverse axis C-C of the fixed stop 62, which this angle α' is about 7-degrees counterclockwise from the transverse axis C-C in the illustrated embodiment. Thus, in the illustrated embodiment, the extension arm 16 and hub 34 are rotatable about the shaft 14 and axis A-A by about 374-degrees (the first rotation range of 342-degrees plus the second rotation range of 32-degrees).

As will be appreciated, the minimum range of total rotation of the extension arm 16 and hub 34 about the shaft 14 and axis A-A may be 360-degrees or greater than 360-degrees, or even up to just less than 720-degrees (e.g. 710-degrees) if the angular spans of the floating stop 42, cavity 44, and fixed stop 62 components so permit. As noted above, this total rotation range may be a compound of the first and second rotation ranges. Where the floating stop 42 is in engagement with the first contact face 46 when the floating stop engages the second stop surface 52, the arm will have rotated the maximum of the first rotation range and a minimum or none of the second rotation range. Likewise, where the floating stop 42 is in engagement with the second contact face 48 when the floating stop engages the second stop surface 52, then the arm will have rotated the maximum of the first rotation range and the maximum of the second rotation range, such as shown in FIG. 9. Similarly, where the floating stop 42 is not in engagement with either contact face 46 or 48, then the arm will have rotated in the middle of the second rotation range. Generally, each of the first and second rotation ranges enable greater than 0-degrees of rotation to enable the at least 360-degrees of rotation of the extension arm 16 about the shaft 14. It is of course further understood that the rotational control mechanism 40 may be modified to provide less than 360-degree total rotation, such as by increasing the angular spans of the floating stop 42 and/or fixed stop 62; or adding additional fixed stops 62.

In exemplary embodiments, the elongated cavity 44 forms an arcuate segment defined by an angular span between the opposite first and second contact faces 46, 48 that may be in a range from about 1-degree to about 180-degrees, and even more particularly from about 10-degrees to about 60-degrees, such as about 45-degrees in the illustrated embodiment. In exemplary embodiments, the angular span between the first and second stop surfaces 50, 52 (e.g., width of fixed stop 62) may be in a range from about 1-degree to about 45-degrees, even more particularly between 1-degree and 20-degrees, such as about 5-degrees in the illustrated embodiment. In exemplary embodiments, the floating stop 42 may have an angular span in a range from about 1-degree to about 45-degrees, even more particularly between 1-degree and 20-degrees, such as about 13-degrees in the illustrated embodiment. In exemplary embodiments, the at least 360-degrees range provided by the rotational control mechanism 40 may be in a range from 360-degrees to less than 720-degrees, more particularly from 360-degrees to 540-degrees, and even more particularly from 360-degrees to 450-degrees, such as about 374-degrees in the illustrated embodiment.

Figure 10:
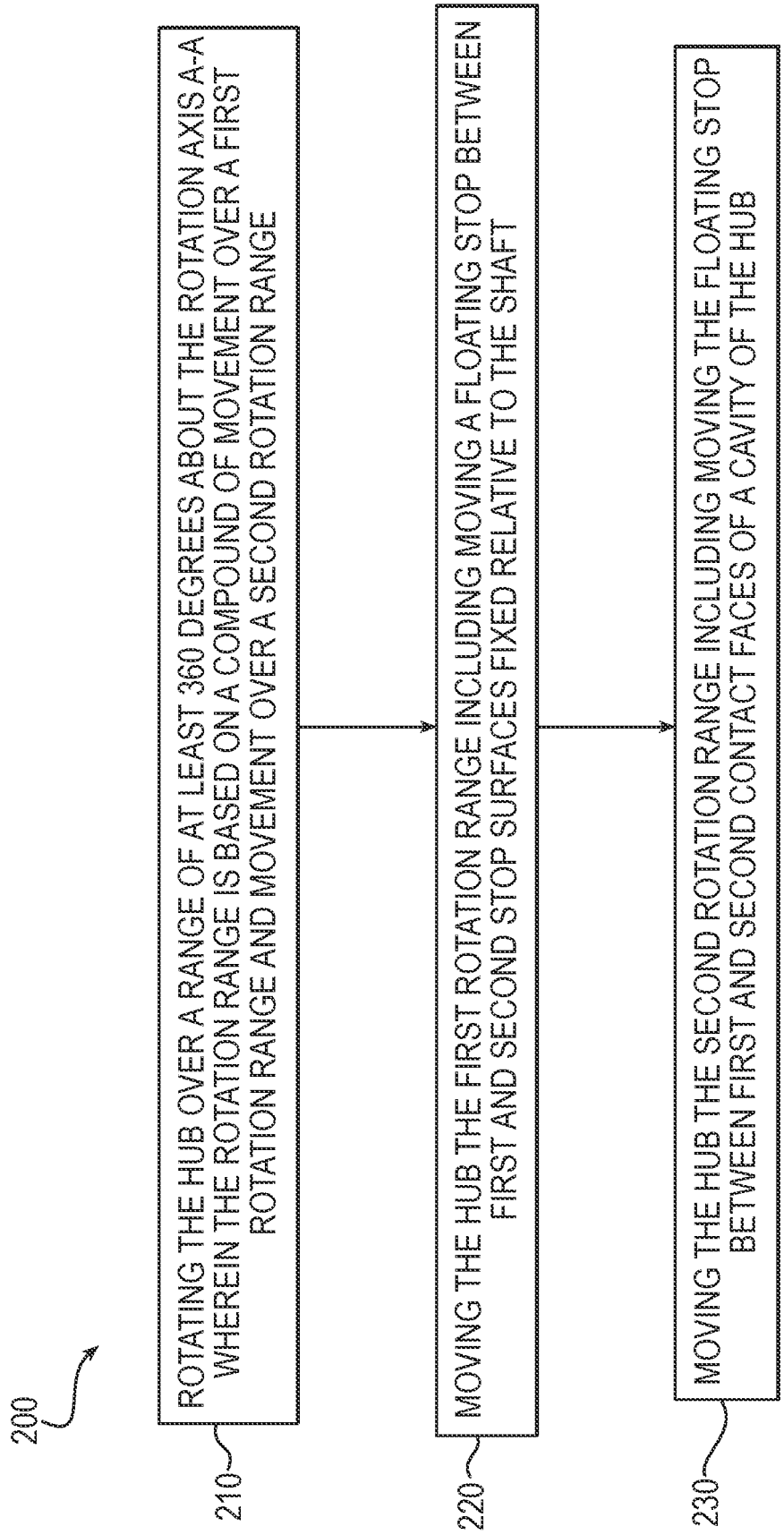
FIG. 10 shows a flowchart of a method of operating the medical device support system of FIG. 1.

Referring now to FIG. 10, there is shown a flowchart 200 of the exemplary method of rotating an extension arm about a shaft of a medical device support system, such as for the medical device support system 10 shown in FIG. 1. The method includes at step 210 rotating a hub of the shaft over a range of at least 360-degrees about a rotation axis of the shaft, wherein the rotation range is based on a compound of movement over a first rotation range and movement over a second rotation range. At step 220, the method includes moving the hub the first rotation range including moving a floating stop between first and second stop surfaces fixed relative to the shaft. At step 230, the method includes moving the hub the second rotation range including moving the floating stop between first and second contact faces of a cavity of the hub.

Figure 11:
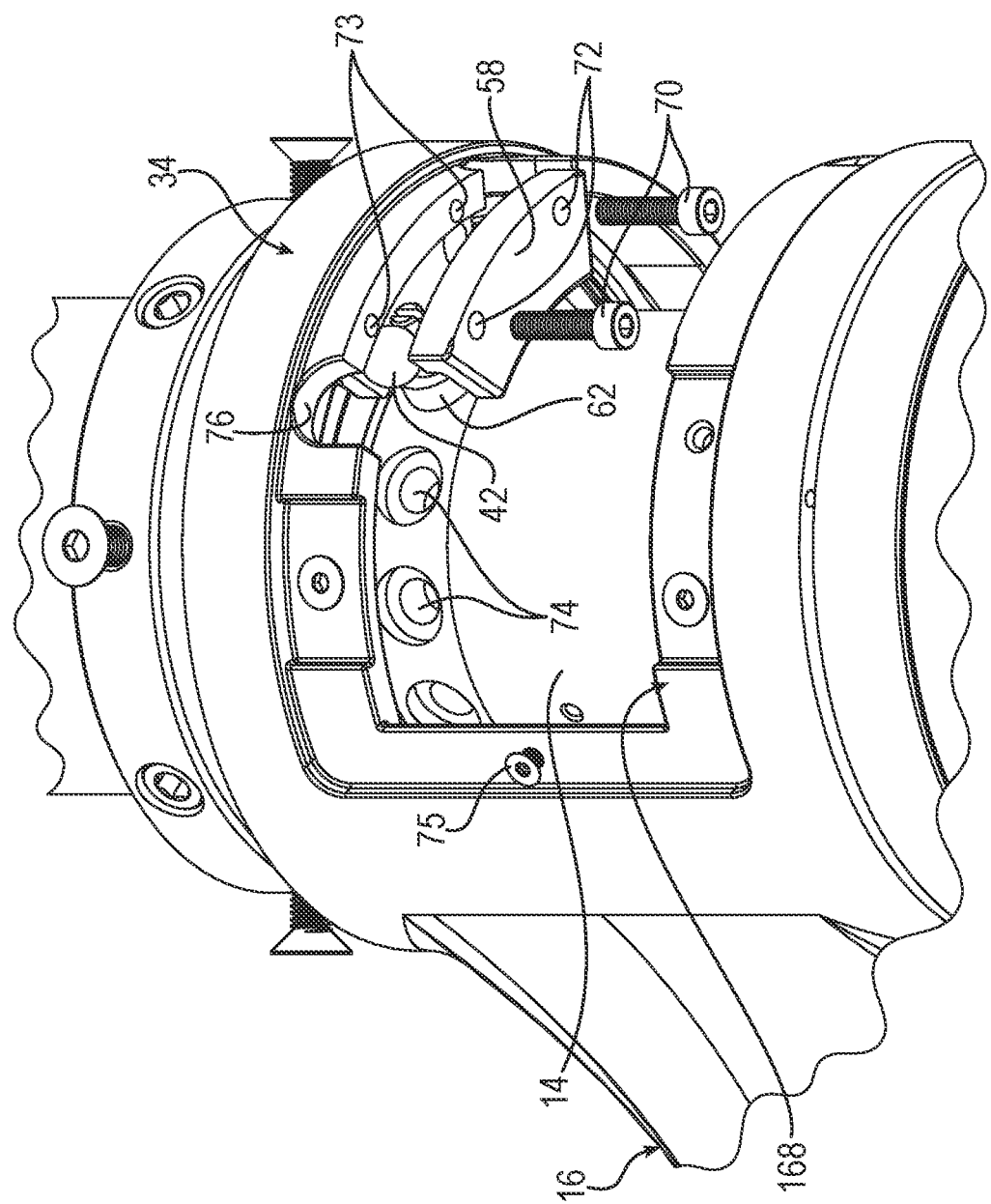
FIG. 11 is a partially exploded bottom, front, left isometric view of another exemplary shaft and extension arm hub connection, including another exemplary rotational control mechanism, similarly to that shown in FIG. 3, and further showing an assembly operation of the rotational control mechanism.

Turning to FIG. 11, an exemplary method of assembling a medical device support system 10, and more particularly a rotational control mechanism 40, is shown. The medical device support system 10 and the rotational control mechanism 40 is substantially the same as that described above in connection with FIGS. 1-9, except that the portions of the hub 34 defining the elongated cavity 44 are illustrated as a multi-part assembly structure for facilitating assembly and/or maintenance of the system 10. Consequently, the same reference numerals are used to denote structures corresponding to the same or substantially similar structures between the system shown in FIG. 11 and the system shown in FIG. 1. Moreover, the foregoing description of the system 10 in FIGS. 1-9 is equally applicable to the system 10 in FIG. 11, except as noted below.

As shown in the illustrated embodiment, the lower wall 58 for forming the elongated cavity 44 and supporting the floating stop 42 (e.g., ball) is couplable to another portion of the hub 34 via suitable fasteners, such as screws 70, which are received in suitable receivers 72 in the lower wall 58 (e.g., through bores) and in receivers 73 in the receiving portion of the hub 34 (e.g., threaded bores). This enables ease of assembly for enclosing the floating stop 42 within the cavity 44, and also may enable improved maintenance, such as for lubricating surfaces in the cavity and/or replacing the floating stop 42 due to wear. It is understood, however, that other assembly methods may be employed. For example, in the illustrative embodiment of FIG. 1, the cavity 44 may be formed by a unitary surfaces of the hub 34, such as by additive manufacturing, in which the floating stop 42 is additively manufactured and enclosed within the cavity 44 during the additive manufacturing process. Alternatively, a window or other access opening could be employed for placing the floating stop 42 (e.g., ball) within the cavity 44. Generally, as would be understood by those having ordinary skill in the art, one or more portions of the hub 34 forming the cavity 44 may be unitary with other portions of the hub 34; or one or more surfaces supporting and/or containing the floating stop 42 may be operatively attached to portions of the hub 34 in any suitable manner.

Similarly to the system 10 described above in connection with FIGS. 1-9, the system 10 shown in FIG. 11 includes a plurality of angularly (circumferentially) spaced apart receivers 74 in the shaft 14, such as bore holes, that are configured to receive the fixed stop 62 (e.g., pin). Any suitable number of receivers 74 in any suitable configuration may be provided for securing the fixed stop 62, either removably/adjustably or non-removably/non-adjustably, relative to the shaft 14. This enables greater flexibility in the design of system 10. For example, where the system 10 is installed in a particular position within the room, such as near a corner or near other equipment, the ability to selectively decide the rotational path of the extension arm 16 during assembly provides greater flexibility during the assembly process. Moreover, the ability to adjust such rotational positions by adjusting the location of the fixed stop 62 about the shaft 14 enables improved flexibility, such as when the room layout is modified, without having to relocate the entire system 10. Moreover, the multiple locations of the receivers 74 also may enable multiple fixed stops 62 to be employed in the system 10, such as where less than the full rotational range enabled by the rotational control mechanism 40 is desired, such as for limiting the rotational travel to only 360-degrees, or even less than 360-degrees. Such possibilities greatly enhance the flexibility the system design.

Briefly turning back to FIG. 7, for example, twelve such receivers 74 are provided in evenly spaced apart positions (e.g., 30-degrees apart) about the shaft 14 for receiving the fixed stop 62. In the illustrated embodiment, the receivers 74 are configured as counter-sunk threaded bores in which the fixed stop 62 (e.g., threaded pin) may be threaded into the threaded bore. Alternatively, the bores may be through holes and the fixed stop may be press fit into the bores. In either case, the position of the fixed stop(s) 62 are removable and selectively adjustable to control the rotational movement of the extension arm 16 and hub 34 relative to the shaft 14.

Again referring to FIG. 11, and similarly to the system 10 in FIGS. 1-9, to facilitate assembly and/or adjustment of the rotational control mechanism 40, the hub 34 includes opening 168, such as a window, which may be covered by a suitable cover (not shown) and fastened with suitable fasteners, such as screws 75. As shown, the hub 34 also may include at least one notched portion 76, or cutout, for facilitating insertion and/or removal of the fixed stop 62 during assembly and/or adjustment of the rotational control mechanism 40. The notched portion(s) 76 are circumferentially offset from the cavity 44, and axially align with the location of the receivers 74 in the shaft 14. This is because, in the illustrated embodiment, the hub 34 generally may be axially constrained once installed on the shaft 14.

Figure 12:
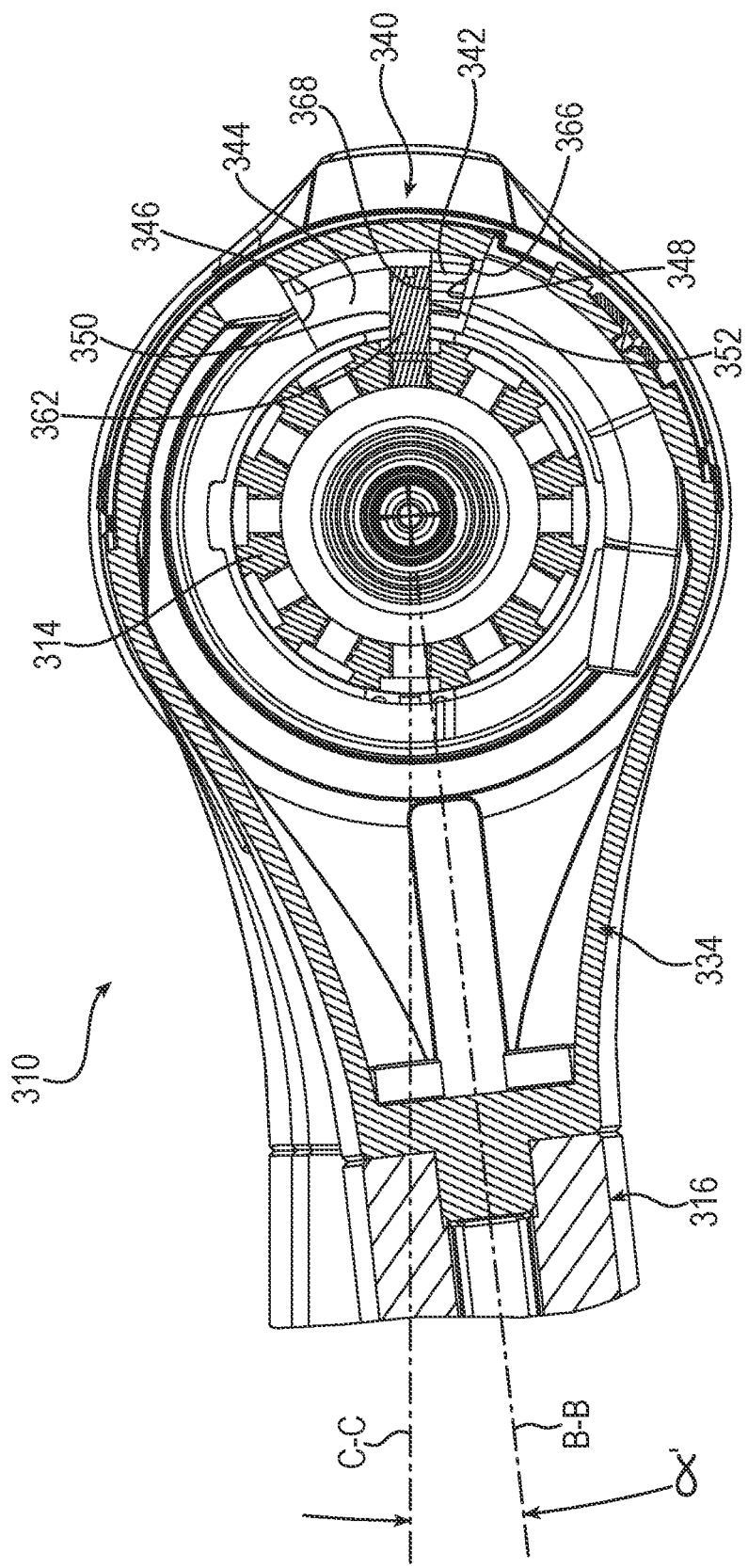
FIG. 12 shows a top cross section view of another exemplary rotational control mechanism of a medical device support, showing a maximum counterclockwise position of the rotational control mechanism, similarly to that shown in FIG. 9, except with a different configuration of an exemplary floating stop.

Turning now to FIG. 12, another exemplary embodiment of a medical device support system 310 including an exemplary rotational control mechanism 340 is shown. The system 310 and rotational control mechanism 340 is substantially the same as the above-referenced medical device support system 10 and rotational control mechanism 40, except that the floating stop 342 in the illustrated embodiment of FIG. 12 is configured in a polyhedron shape and surfaces of the hub 334 and/or fixed stop 362 are configured complimentary to the floating stop 342. Consequently, the same reference numerals but indexed by 300 are used to denote structures corresponding to similar structures in the systems 10, 310. In addition, the foregoing description of the system 10 is equally applicable to the system 310, except as noted below. Moreover, it will be appreciated upon reading and understanding the specification that aspects of the systems 10, 310 may be substituted for one another or used in conjunction with one another where applicable.

Similarly to the system 10, the system 310 includes a shaft 314, at least one extension arm 316 having a support for a medical device, and a hub 334 at a proximal end of the extension arm 316 and mounted to the shaft 314 for pivotable movement about a rotation axis A-A of the shaft 314. The rotational control mechanism 340 of the system 310 includes at least one floating stop 342 movably disposed in an elongated cavity 344 of the hub 334, and which interacts with first and second contact faces 346, 348 of the hub, and with first and second stop surfaces 350, 352 fixed relative to the shaft 314, for providing the range of at least 360-degrees rotation of the extension arm 316 about a rotation axis A-A of the shaft 314.

As shown, the polyhedron shape of the floating stop 342 is in a wedge shape such that first and second engagement surfaces 366, 368 of the floating stop 342 compliment (with the same angles) the contact faces 346, 348 forming the ends of the cavity 344 and/or the stop surfaces 350, 352 forming opposite sides of the fixed stop 362. This enables improved contact area as the floating stop 342 moves between contact faces 346, 348 during rotation of the hub 334 about the axis A-A, as described in detail above.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A medical device support system, comprising:
   a shaft;
   an extension arm having a support for a medical device;
   a hub at a proximal end of the extension arm and mounted to the shaft for pivotable movement of the extension arm and the hub about a rotation axis of the shaft, the hub having an elongated cavity including first and second contact faces; and at least one floating stop movably disposed in the elongated cavity of the hub between the first and second contact faces;
wherein the hub is pivotably mounted for a range of at least 360-degrees rotation about the rotation axis, wherein the at least 360-degrees rotation range is based on a compound of a first rotation range and a second rotation range, wherein the first rotation range is defined by a first movable amount of the at least one floating stop between first and second stop surfaces fixed relative to the shaft, and wherein the second rotation range is defined by a second movable amount of the at least one floating stop between the first and second contact faces of the hub.

2. The medical device support system of claim 1, wherein the at least one floating stop interfacing with one of the first or second stop surfaces of the shaft and one of the first or second contact faces of the hub restricts rotation of the hub about the rotation axis beyond the at least 360-degrees rotation range.

3. The medical device support system of claim 1, wherein the hub is pivotably mounted for the at least 360-degrees rotation from a first stop position to a second stop position and vice versa, wherein at the first stop position, the at least one floating stop interfaces with one of the first or second stop surfaces fixed relative to the shaft and one of the first or second contact faces of the hub to limit further counterclockwise rotation of the hub about the rotation axis, and at the second stop position, the at least one floating stop interfaces with an opposite one of the first or second stop surfaces and an opposite one of the first and second contact faces of the hub to limit further clockwise rotation of the hub about the rotation axis.

4. The medical device support system of claim 3, wherein the at least one floating stop is sandwiched between the first stop surface and the first contact face at the first stop position, and wherein the at least one floating stop is sandwiched between the second stop surface and the second contact face at the second stop position.

5. The medical device support system of claim 1, wherein the first movable amount of the at least one floating stop is determined by an amount of movement of the at least one floating stop rotating at least partially about the rotation axis from a first stop position, in which the at least one floating stop engages both the first stop surface and the first contact face, to an intermediate position, in which the at least one floating stop engages the second stop surface, and
wherein the second movable amount of the at least one floating stop is determined by an amount of movement of the at least one floating stop rotating at least partially about the rotation axis from the intermediate position to a second stop position, in which the at least one floating stop engages both the second stop surface and the second contact face.

6. The medical device support system of claim 5, wherein the second stop surface is configured to move the at least one floating stop within the cavity from the intermediate position to the second stop position.

7. The medical device support system of claim 1, wherein the first and second stop surfaces are formed by opposite sides of at least one fixed stop radially outwardly protruding from an outer surface of the shaft, the at least one fixed stop being non-rotatable about the rotation axis.

8. The medical device support system of claim 1, wherein the at least one floating stop includes a spherical ball.

9. The medical device support system of claim 1, wherein the elongated cavity is formed by radially inwardly projecting surfaces of the hub that at least partially enclose the at least one floating stop.

10. The medical device support system of claim 9, wherein the radially inwardly projecting surfaces of the hub form a radially inwardly projecting lug, and wherein the first and second contact faces of the hub form opposite end portion surfaces of the lug.

11. The medical device support system of claim 1, wherein the first and second stop surfaces radially overlap with the first and second contact faces of the hub, and radially overlap with the at least one floating stop; and
wherein the first and second contact faces include respective openings for receiving the first and/or second stop surfaces, thereby enabling the first or second stop surface to move the at least one floating stop within the elongated cavity between the first and second contact faces.

12. The medical device support system of claim 1, wherein the first and second stop surfaces radially overlap with opposite first and second engagement surfaces of the at least one floating stop, and wherein the first and second stop surfaces and the opposite first and second engagement surfaces of the at least one floating stop lie in the same plane that is perpendicular to the rotation axis.

13. The medical device support system of claim 1, wherein the first movable amount less than 360-degrees, and wherein the second movable amount is in a range from 1-degree to less than 180-degrees.

14. The medical device support system of claim 1, wherein the at least 360-degrees rotation range is less than 540-degrees.

15. The medical device support system of claim 1, wherein the first and second stop surfaces are formed by opposite sides of a fixed stop, and wherein the shaft includes a plurality of receivers evenly spaced about the rotation axis of the shaft for receiving the fixed stop.

16. The medical device support system of claim 1, wherein the shaft has an axial hollow and a radial aperture and wherein the cavity of the hub is positioned to allow passage of electrical and communication lines through the axial hollow, through the radial aperture, and into a longitudinally extending cavity in the extension arm.

17. The medical device support system of claim 16, wherein the hub of the extension arm includes upper and lower pivot bearings configured to pivotably engage the hub with the shaft, and a radial opening positioned axially between the upper and lower pivot bearings, and wherein the cavity of the hub is positioned to allow passage of the electrical and communication lines between the upper and lower pivot bearings, through the radial opening of the hub, and into the longitudinally extending cavity in the extension arm.

18. A medical device support system, comprising:
a shaft;
an extension arm having a support for a medical device;
a hub at a proximal end of the extension arm and mounted to the shaft for pivotable movement of the extension arm and the hub about a rotation axis of the shaft, wherein the hub includes an elongated cavity having first and second contact faces;
at least one floating stop disposed in the cavity and being movable between the first and second contact faces; and first and second stop surfaces fixed relative to the shaft and radially extending to overlap with a rotation path of the at least one floating stop;

wherein the hub is pivotably mounted for a range of at least 360-degrees rotation about the rotation axis from a first stop position to a second stop position and vice versa, wherein at the first stop position, the first stop surface engages a first engagement surface of the at least one floating stop and an opposite second engagement surface of the at least one floating stop engages the first contact face of the cavity, thereby limiting further counterclockwise rotation of the hub about the rotation axis, and wherein at the second stop position, the second stop surface engages the second engagement surface of the at least one floating stop and the opposite first engagement surface of the at least one floating stop engages the second contact face of the cavity, thereby limiting further clockwise rotation of the hub about the rotation axis.

19. The medical device support system of claim 18, wherein the at least one floating stop is configured to move with the hub about the rotation axis from the first stop position to an intermediate position between the first and second stop positions, wherein at the intermediate position the at least one floating stop engages with the second stop surface; and wherein the second stop surface is configured to move the at least one floating stop within the elongated cavity from the intermediate position to the second stop position.

20. A method of rotating an extension arm about a shaft of a medical device support system, the extension arm having a support for a medical device and a hub at its proximal end mounted to the shaft for pivotable movement about a rotation axis of the shaft, the method comprising:

rotating the hub over a range of at least 360-degrees about the rotation axis, wherein the at least 360-degrees rotation range is based on a compound of movement over a first rotation range and movement over a second rotation range, wherein movement over the first rotation range includes moving at least one floating stop of the hub between first and second stop surfaces fixed relative to the shaft, and wherein movement over the second rotation range includes moving the at least one floating stop with the first or second stop surface between first and second contact faces of an elongated cavity of the hub.

* * * * *